US011337923B2

(12) United States Patent
Yu

(10) Patent No.: US 11,337,923 B2
(45) Date of Patent: May 24, 2022

(54) NANOLIPOSOME-MICROBUBBLE CONJUGATE INCLUDING DRUG FOR HAIR LOSS TREATMENT ENCAPSULATED IN NANOLIPOSOME AND COMPOSITION FOR ALLEVIATING OR TREATING HAIR LOSS CONTAINING SAME

(71) Applicant: MOOGENE MEDI CO., LTD., Seongnam-si (KR)

(72) Inventor: Kyeong Nam Yu, Seongnam-si (KR)

(73) Assignee: MOOGENE MEDI CO., LTD., Seongnam-si (KR)

( * ) Notice: Subject to any disclaimer, the term of this patent is extended or adjusted under 35 U.S.C. 154(b) by 0 days.

(21) Appl. No.: 16/646,887

(22) PCT Filed: Apr. 11, 2019

(86) PCT No.: PCT/KR2019/004311
§ 371 (c)(1),
(2) Date: Mar. 12, 2020

(87) PCT Pub. No.: WO2019/245142
PCT Pub. Date: Dec. 26, 2019

(65) Prior Publication Data
US 2021/0106529 A1 Apr. 15, 2021

(30) Foreign Application Priority Data
Jun. 18, 2018 (KR) .................. 10-2018-0069736

(51) Int. Cl.
*A61K 9/127* (2006.01)
*A61P 17/14* (2006.01)
(Continued)

(52) U.S. Cl.
CPC .......... *A61K 9/1271* (2013.01); *A61K 9/1277* (2013.01); *A61K 31/506* (2013.01);
(Continued)

(58) Field of Classification Search
CPC ..................................................... A61K 9/127
See application file for complete search history.

(56) References Cited

U.S. PATENT DOCUMENTS 5,030,442 A * 7/1991 Uster ................... A61K 9/1272
424/45
5,994,362 A * 11/1999 Gormley ................ A61K 31/58
514/284
(Continued)

FOREIGN PATENT DOCUMENTS

CN 1943541 A 4/2007
CN 106361703 A 2/2017
(Continued)

OTHER PUBLICATIONS

Ritu Malik, Ketan Pancholi, and Andreas Melzer. "Microbubble-liposome conjugate: Payload evaluation of potential theranostic vehicle." Nanobiomedicine, vol. 3, 2016, pp. 1-8 (Year: 2016).*
(Continued)

*Primary Examiner* — Isaac Shomer
(74) *Attorney, Agent, or Firm* — Sughrue Mion, PLLC

(57) ABSTRACT

Provided are a nanoliposome-microbubble conjugate in which a drug for hair loss treatment such as finasteride, minoxidil, dutasteride, etc. is encapsulated in a nanoliposome and a composition for alleviating or treating hair loss containing the same. Since an orally administered agent such as finasteride, currently useful as a drug for hair loss treatment, causes side effects, drug delivery through scalp application is most desirable, but the drug is not delivered to hair follicle cells through scalp application alone. Since a drug for hair loss treatment useful as an external preparation for skin causes various side effects, the concentration thereof that is used needs to be further lowered. The above nanoliposome-microbubble conjugate is capable of increasing the
(Continued)

delivery efficiency of a drug for hair loss treatment at a low concentration, and is thus very effective at treating androgenic alopecia.

11 Claims, 4 Drawing Sheets

(51) Int. Cl.
  *A61K 31/506* (2006.01)
  *A61K 31/58* (2006.01)
  *B82Y 5/00* (2011.01)
  *B82Y 40/00* (2011.01)

(52) U.S. Cl.
  CPC .............. *A61K 31/58* (2013.01); *A61P 17/14* (2018.01); *B82Y 5/00* (2013.01); *B82Y 40/00* (2013.01)

(56) References Cited

U.S. PATENT DOCUMENTS

| | | | |
|---|---|---|---|
| 2012/0231069 A1* | 9/2012 | Nowotnik | A61K 9/5161 424/450 |
| 2014/0314784 A1* | 10/2014 | Bedian | A61K 45/06 424/144.1 |
| 2015/0044284 A1* | 2/2015 | Santus | A61K 9/1652 424/456 |
| 2016/0045499 A1* | 2/2016 | Hsu | A61P 17/10 514/154 |

FOREIGN PATENT DOCUMENTS

| | | | | |
|---|---|---|---|---|
| JP | 2020-535233 | A | 12/2020 | |
| KR | 10-2010-0086560 | A | 8/2010 | |
| KR | 10-1054731 | B1 | 8/2011 | |
| KR | 10-1082391 | B1 | 11/2011 | |
| KR | 10-2014-0018150 | A | 2/2014 | |
| KR | 10-2016-0074883 | A | 6/2016 | |
| KR | 10-1683463 | B1 | 12/2016 | |
| KR | 10-1710026 | B1 | 2/2017 | |
| KR | 10-1870694 | B1 | 6/2018 | |
| WO | WO-2014021678 | A1 * | 2/2014 | ......... A61K 47/6925 |
| WO | 2019/078611 | A1 | 4/2019 | |

OTHER PUBLICATIONS

Sang-Im Lee, et al. "Effect of Charge Carrier Lipid on Skin Penetration, Retention, and Hair Growth of Topically Applied Finasteride-Containing Liposomes." Biomolecules and Therapeutics, vol. 19(2), 2011, pp. 231-236. (Year: 2011).*
Behfar Moghaddam, Sarah E. McNeil, Qinguo Zheng, Afzal R. Mohammed and Yvonne Perrie. "Exploring the Correlation Between Lipid Packaging in Lipoplexes and Their Transfection Efficacy." Pharmaceutics, vol. 3, 2011, pp. 848-864. (Year: 2011).*
Google Patents. English Translation of WO 2014/021678 A1. Accessed at https://patents.google.com/patent/WO2014021678A1/en?oq=dspe-peg-spdp on Oct. 25, 2021, pp. 1-18. Originally published in Korean on Feb. 6, 2014. (Year: 2014).*
Fei Yan et al. "Paclitaxel-liposome-microbubble complexes as ultrasound-triggered therapeutic drug delivery carriers." Journal of Controlled Release 166 (2013) 246-255. (Year: 2013).*
Google Patents. English Translation of CN1943541A. "Supersonic micro bubble skin permeate promotor." https://patents.google.com/patent/CN1943541A/en?oq=CN+1943541 accessed Feb. 7, 2022, originally published in Chinese in 2007, pp. 1-8. (Year: 2007).*
Google Patents. English Translation of CN106361703A. "Finasteride nano-liposome, gel and preparation method thereof." https://patents.google.com/patent/CN106361703A/en?oq=CN+106361703 accessed Feb. 7, 2022, originally published in Chinese in 2017, pp. 1-9. (Year: 2017).*
Young Il Yoon et al. "Ultrasound-Mediated Gene and Drug Delivery Using a Microbubble-Liposome Particle System." Theranostics, vol. 4 Issue 11, 2014, pp. 1133-1144. (Year: 2014).*
Notice of Allowance dated Apr. 13, 2021 from the Japanese Patent Office in Application No. 2020-539667.
Office Action dated Feb. 9, 2021 from the Japanese Patent Office in Application No. 2020-539667.
Seeun Park et al., "Bee Venom Promotes Hair Growth in Association with Inhibiting 5a-Reductase Expression", Biol Pharm Bull, 2016, vol. 39, No. 6, pp. 1060-1068 (9 pages total).
Ai-Ho Liao et al., "Effectiveness of a Layer-by-Layer Microbubbles-Based Delivery System for Applying Minoxidil to Enhance Hair Growth", Theranostics, 2016, pp. 817-827, vol. 6, No. 6.
Dr. Venkataram Mysore, "Finasteride and sexual side effects", Indian Dermatology Online Journal, Jan.-Apr. 2012, pp. 62-65, vol. 3, No. 1.
John A. Zuris et al., "Efficient Delivery of Genome-Editing Proteins In Vitro and In Vivo," Nat. Biotechnol., Jan. 2015, pp. 1-26, vol. 33, No. 1.
International Search Report for PCT/KR2019/004311 dated, Jul. 11, 2019 (PCT/ISA/210).
Communication dated Oct. 21, 2021 from the Australian Patent Office in Australian Application No. 2019290955.
Young Il Yoon et al., "Ultrasound-Mediated Gene and Drug Delivery Using a Microbubble-Liposome Particle System", Theranostics, 2014, vol. 4, Issue 11, pp. 1133-1144 (12 pages total).
Ritu Malik et al., "Microbubble-liposome conjugate: Payload evaluation of potential theranostic vehicle", Nanobiomedicine, 2016, vol. 3, pp. 1-8 (8 pages total).
Ine Lentacker et al., "Ultrasound Exposure of Lipoplex Loaded Microbubbles Facilitates Direct Cytoplasmic Entry of the Lipoplexes", Molecular Pharmaceutics, vol. 6, No. 2, pp. 457-467 (11 pages total).
Azadeh Kheirolomoom et al., "Acoustically-Active Microbubbles Conjugated to Liposomes: Characterization of a Proposed Drug Delivery Vehicle", J Control Release, 2007, vol. 118, No. 3, pp. 275-284—(21 pages total).
Alexander L. Klibanov et al., "Ultrasound-triggered release of materials entrapped in microbubble-liposome constructs: a tool for targeted drug delivery", J Control Release, 2010, vol. 148, No. 1, pp. 13-17 (12 pages total).
Office Action dated Jul. 14, 2021 in Chinese Application No. 201980004836.X.

* cited by examiner

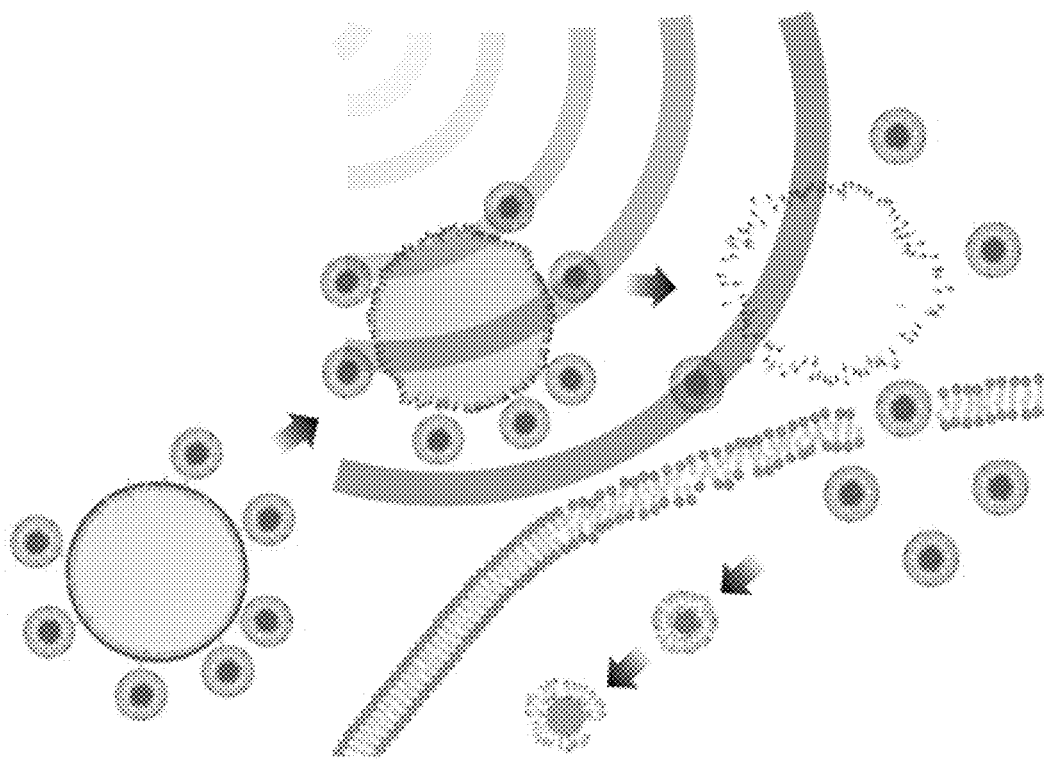
[Fig. 1]

[Fig. 2]
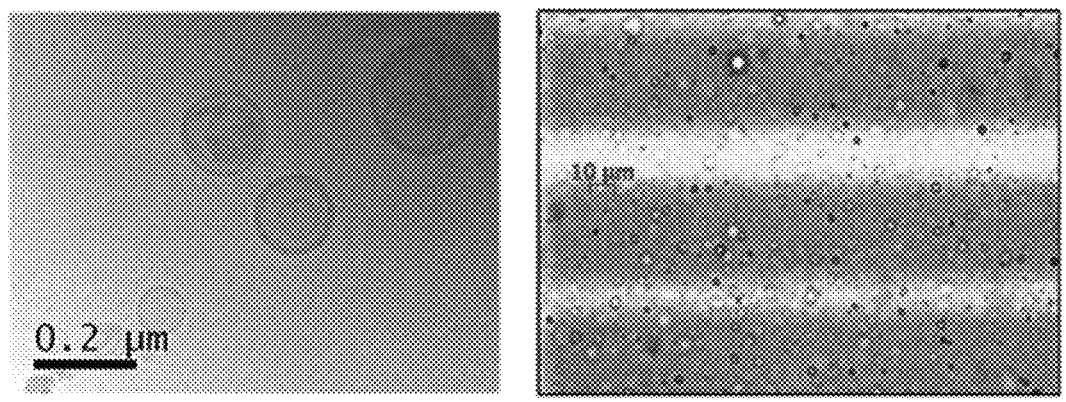
[Fig. 3]
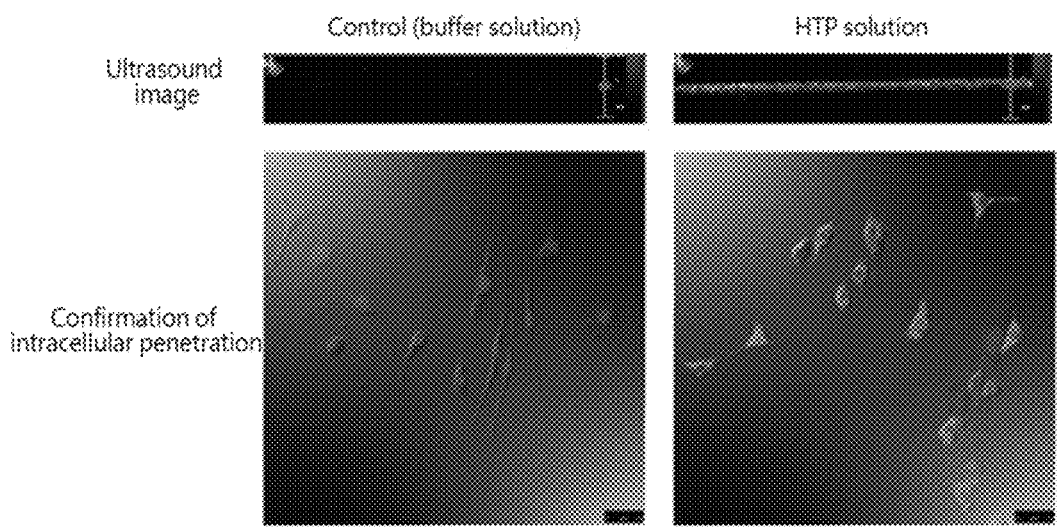

[Fig. 4]
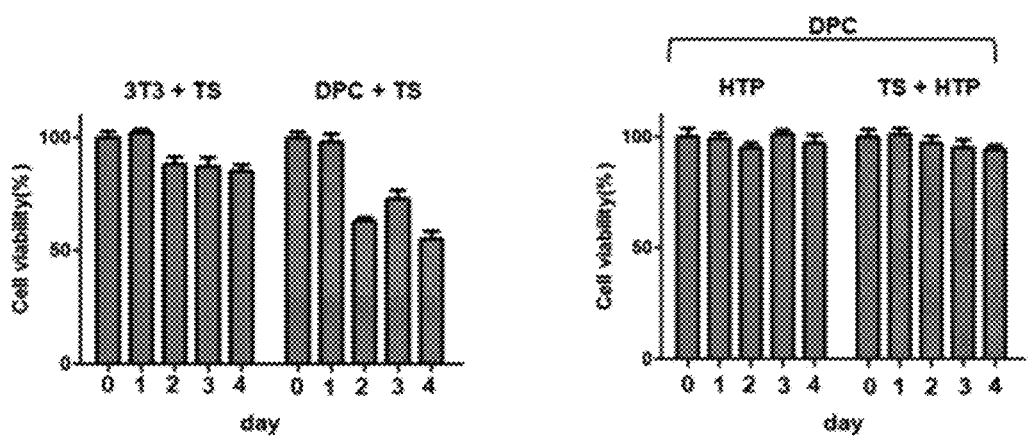

[Fig. 5]
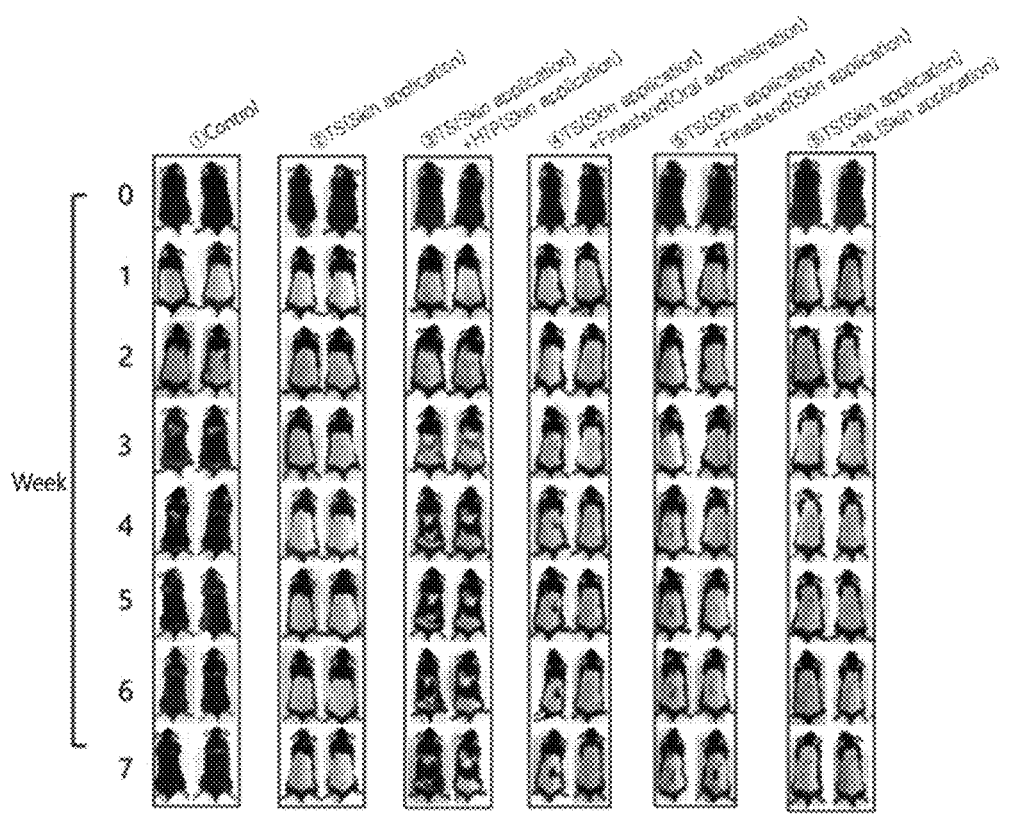

NANOLIPOSOME-MICROBUBBLE CONJUGATE INCLUDING DRUG FOR HAIR LOSS TREATMENT ENCAPSULATED IN NANOLIPOSOME AND COMPOSITION FOR ALLEVIATING OR TREATING HAIR LOSS CONTAINING SAME

CROSS REFERENCE TO RELATED APPLICATIONS

This application is a National Stage of International Application No. PCT/KR2019/004311 filed Apr. 11, 2019, claiming priority based on Korean Patent Application No. 10-2018-0069736 filed Jun. 18, 2018, the entire contents of which are incorporated herein by reference.

TECHNICAL FIELD

The present invention relates to a nanoliposome-microbubble conjugate in which a drug for hair loss treatment is encapsulated in a nanoliposome and to a composition for alleviating or treating hair loss containing the same.

More particularly, the present invention relates to a nanoliposome-microbubble conjugate, in which a nanoliposome including a drug for hair loss treatment such as finasteride, minoxidil, dutasteride, etc. encapsulated therein is chemically stably conjugated to a microbubble including a hydrophobic gas therein, and to a composition for alleviating or treating hair loss containing the same.

BACKGROUND ART

Hair loss generally refers to the loss of thick black hair from the scalp. The causes of hair loss are various, but genetics and the male hormone androgen are considered to be important factors. Of these, androgenic alopecia, which accounts for about 60 to 70% of hair loss, progresses in a manner in which testosterone is converted into dihydrotestosterone (DHT) by 5-alpha reductase (SRD5A) and excessively produced dihydrotestosterone binds to the androgenic receptor (AR) of dermal papilla cells (DPCs) to thus induce apoptosis, leading to hair loss due to shrinkage of the hair. Since men with high expression of 5-alpha reductase, particularly 5-alpha reductase type 2 (SRD5A2), which is mainly distributed in the dermal papillae and outer root sheath of hair follicles, or persons having high activity of 5-alpha reductase type 2 have a quite large amount of dihydrotestosterone compared to most men, the possibility of hair loss is increased. Hence, the main treatment for androgenic alopecia is to lower the amount or activity of 5-alpha reductase type 2 in order to prevent the conversion of testosterone into dihydrotestosterone.

Drugs currently developed as therapeutic agents for hair loss include Propecia, minoxidil, dutasteride, and the like. Propecia, containing finasteride, functions to directly inhibit 5-alpha reductase type 2, and dutasteride functions to inhibit 5-alpha reductase type 1 and type 2 to thus prevent the conversion of testosterone into dihydrotestosterone, thereby slowing the progression of hair loss. Finasteride is an oral drug for hair loss treatment, which was originally used to treat prostatic hypertrophy and in which side effects of hair growth were observed in patients taking the same, leading to later development as an androgenic alopecia therapeutic agent. However, side effects such as loss of libido, erectile dysfunction, etc. occur in patients who take such a drug, and hair loss resumes when administration of the drug is discontinued. In particular, the USFDA recommends that men with infertility or low sperm counts stop taking the drug (Myscore V et al., 2012).

Meanwhile, two important properties required of intracellular drug delivery systems are efficiency and cytotoxicity (safety), and carrier technology of nanoliposomes composed of cholesterols or lipids is widely used (Zuris J A et al., 2015). However, such nanoliposome technology alone does not facilitate drug delivery into the dermis, which is present below the stratum corneum, which acts as a skin barrier (Nemes Z et al., 1999).

A microbubble, which is an FDA-approved diagnostic ultrasound contrast agent, is provided in the form of a micro-sized bubble filled with a hydrophobic gas. A microbubble technique causes cavitation when the microbubble is exposed to ultrasound to thus temporarily form pores in the cell membranes of surrounding cells, whereby the nanoliposome may be effectively delivered into the cells using sonoporation, through which a material penetrates cells through the pores thus formed, unlike other cell delivery methods.

Therefore, the present inventors have prepared a composition in which finasteride is encapsulated in a nanoliposome and the nanoliposome is conjugated to a microbubble in order to efficiently deliver the nanoliposome including finasteride encapsulated therein to the dermal layer. Thereby, a carrier having good drug delivery efficiency into the dermis is manufactured and used as a composition for alleviating or treating hair loss, thus culminating in the present invention.

CITATION LIST

Patent Literature (Patent Document 1) Korean Patent No. 10-1683463 (Invention Title: Microbubble-liposome-melanin nanoparticle complex and contrast agent comprising the same, Applicant: Seoul National University Industry-Academic Cooperation Foundation, Registration Date: Dec. 1, 2016)

(Patent Document 2) Korean Patent No. 10-1082391 (Invention Title: Nanohybrid composite comprising vitamin C for preventing hair loss and enhancing hair restoration and composition for enhancing hair restoration, Applicant: CNPharm Co. Ltd. and Ewha Womans University Industry-Academic Cooperation Foundation, Registration Date: Nov. 4, 2011)

(Patent Document 3) Korean Patent No. 10-1054731 (Invention Title: Nanoparticles containing non-soluble finasteride for hair-growth-promoting compounds and skin external composition comprising the same, Applicant: AmorePacific Corp., Registration Date: Aug. 1, 2011)

Non-Patent Literature (Non-Patent Document 1) Myscore V et al., Finasteride and sexual side effects, Indian Dermatol. Online J, 2012, 3(1), 62-65.

(Non-Patent Document 2) Zuris J A et al., Cationic lipid-mediated delivery of proteins enables efficient protein-based genome editing in vitro and in vivo, Nat. Biotechnol., 2015, 33(1), 73-80. 1. Korean Patent No. 10-1452397

DISCLOSURE

Technical Problem

An objective of the present invention is to provide a nanoliposome-microbubble conjugate in which a drug for hair loss treatment is encapsulated in a nanoliposome and a composition for alleviating or treating hair loss containing the same.

More specifically, an objective of the present invention is to provide a nanoliposome-microbubble conjugate, in which a nanoliposome including a drug for hair loss treatment such as finasteride, minoxidil, dutasteride, etc. encapsulated therein is chemically stably conjugated to a microbubble including a hydrophobic gas therein, and a composition containing the same, which is very effective at alleviating or treating hair loss while avoiding side effects of oral administration.

Technical Solution

The present invention pertains to a nanoliposome-microbubble conjugate, in which a drug for hair loss treatment is encapsulated in a nanoliposome.

The drug for hair loss treatment may include at least one selected from the group consisting of finasteride, minoxidil and dutasteride.

Moreover, the drug for hair loss treatment may inhibit the expression or activity of 5-alpha reductase type 2 to thus prevent the conversion of testosterone into dihydrotestosterone, or may inhibit the death of dermal papilla cells.

The nanoliposome may include lecithin, cholesterol and a cationic phospholipid.

The microbubble may include an amphoteric phospholipid, an anionic phospholipid, cholesterol, a cationic phospholipid and a disulfide-group-containing lipid.

The nanoliposome-microbubble conjugate may have a particle size of 1100 to 2100 nm.

The present invention may provide a composition for alleviating or treating hair loss containing the nanoliposome-microbubble conjugate.

In addition, the present invention provides a method of preparing a nanoliposome-microbubble conjugate capable of selectively recognizing dermal papilla cells as described below. More preferably, the nanoliposome-microbubble conjugate is prepared by separately preparing a nanoliposome and a microbubble and then mixing them.

The nanoliposome may be prepared as follows.

Preferably, the nanoliposome is prepared by: 1) preparing a lipid film composition by mixing lecithin, cholesterol and a cationic phospholipid in chloroform;

2) adding the lipid film composition with a drug solution for hair loss treatment and performing sonication;

3) subjecting the sonicated lipid film composition to freezing and thawing and then to sonication; and 4) centrifuging the lipid film composition sonicated in step 3 and recovering a nanoliposome that is precipitated.

Also, the microbubble may be prepared as follows.

The microbubble may be prepared by:

A) preparing a lipid film composition by mixing an amphoteric phospholipid, cholesterol, an anionic lipid, an amine-group-containing lipid and a disulfide-group-containing lipid in chloroform;

B) adding a glucose solution to step A and performing sonication;

C) subjecting the lipid film composition sonicated in step B to freezing and thawing and then to sonication; and D) preparing a microbubble by introducing a hydrophobic gas into the lipid film composition sonicated in step C.

A nanoliposome-microbubble conjugate may be formed by mixing the microbubble thus prepared with the nanoliposome.

Hereinafter, a detailed description will be given of the present invention.

The present invention is directed to a nanoliposome-microbubble conjugate in which a drug for hair loss treatment is encapsulated in a nanoliposome and to a composition for alleviating or treating hair loss containing the same.

The drug for hair loss treatment may be selected from among finasteride, minoxidil, and dutasteride, and any drug for hair loss treatment that has the same mechanism as these drugs may be used. Moreover, any drug for hair loss treatment may be used, so long as it is able to inhibit the expression or activity of 5-alpha reductase type 2 to thus prevent the conversion of testosterone into dihydrotestosterone.

The nanoliposome may include lecithin ($\alpha$-phosphatidylcholine), a cationic phospholipid and cholesterol, thereby forming a membrane that constitutes a nanoliposome from the lecithin, cationic phospholipid and cholesterol.

Lecithin is widely distributed in animals/plants and has excellent biocompatibility, and the stability thereof has been previously verified, and thus lecithin is broadly useful in food and medicine carrier techniques. Furthermore, it may be used as a material that facilitates control of the size and change of the shape of the nanoliposome.

The cationic phospholipid may include at least one selected from the group consisting of dioleoyl phosphatidylethanolamine (DOPE), 1,2-diphytanoyl-sn-glycero-3-phosphoethanolamine (DPhPE), 1,2-distearoyl-sn-glycero-3-phosphoethanolamine (DSPE), 1,2-dipalmitoyl-sn-glycero-3-phosphoethanolamine (DPPE) and 1,2-dioleoyl-sn-glycero-3-phosphocholine (DOPC). Preferably useful is 1,2-dipalmitoyl-sn-glycero-3-phosphoethanolamine (DPPE).

The nanoliposome of the present invention may be stably dispersed in neutral water, cell broth, blood or the like for several hours or more.

The microbubble of the present invention may include an amphoteric phospholipid, an anionic phospholipid, cholesterol, a cationic phospholipid and a disulfide-group-containing lipid, and is prepared by forming a membrane that constitutes the bubble through the hydrophobic gas introduced into the lipid film composition comprising the mixture thereof.

The amphoteric phospholipid may be selected from the group consisting of 1,2-dipalmitoyl-sn-glycero-3-phosphocholine (DPPC), 1,2-distearoyl-sn-glycero-3-phosphocholine (DSPC), 1,2-dimyristoyl-sn-glycero-3-phosphocholine (DMPC), 1,2-dioleoyl-sn-glycero-3-phosphocholine (DOPC), 1-myristoyl-2-palmitoyl-sn-glycero-3-phosphocholine (MPPC) and 1-myristoyl-2-stearoyl-sn-glycero-3-phosphocholine (MSPC). Preferably, 1,2-dipalmitoyl-sn-glycero-3-phosphocholine (DPPC) is used.

The anionic phospholipid may include at least one selected from the group consisting of dicetyl phosphate (DCP), 1,2-dierucoyl-sn-glycero-3-phosphate (DEPA), 1,2-dilauroyl-sn-glycero-3-phosphate (DLPA), 1,2-dimyristoyl-sn-glycero-3-phosphate (DMPA) and 1,2-dioleoyl-sn-glycero-3-phosphate (DOPA). Preferably, dicetyl phosphate (DCP) is used.

As the cationic phospholipid, the same cationic phospholipid used for the preparation of the nanoliposome may be used, and more specifically, the cationic phospholipid may include at least one selected from the group consisting of dioleoyl phosphatidylethanolamine (DOPE), 1,2-diphytanoyl-sn-glycero-3-phosphoethanolamine (DPhPE), 1,2-distearoyl-sn-glycero-3-phosphoethanolamine (DSPE), 1,2-dipalmitoyl-sn-glycero-3-phosphoethanolamine (DPPE)

and 1,2-dioleoyl-sn-glycero-3-phosphocholine (DOPC). Preferably, 1,2-dipalmitoyl-sn-glycero-3-phosphoethanolamine (DPPE) is used.

The disulfide-group-containing lipid may be exemplified by 1,2-distearoyl-sn-glycero-3-phosphoethanolamine-N-poly(ethylene glycol)-2000-N-[3-(2-pyridyldithio)propionate, also called DSPE-PEG-sPDP.

* DSPE-PEG-sPDP 1,2-distearoyl-sn-glycero-3-phosphoethanolamine-
N-poly(ethyleneglycol)-2000-N-[3-(2-pyridyldithio)propionate The DSPE-PEG-sPDP lipid is a lipid having the chemical structure of Chemical Formula 1 below.

[Chemical Formula 1]

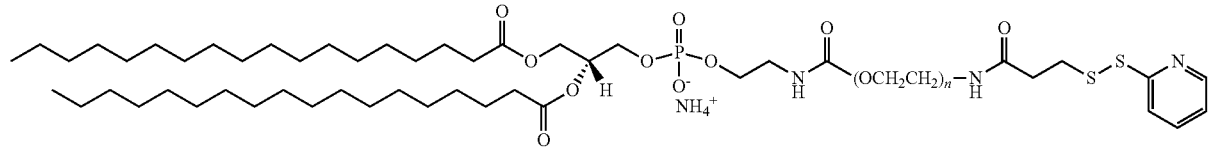

For the preparation of the microbubble, the mixing ratio of the amphoteric phospholipid to the anionic phospholipid to the cholesterol to the cationic phospholipid to the disulfide-group-containing lipid may be 1-3 mM: 0.1-0.3 mM: 0.5-2 mM: 0.1-0.3 mM: 0.1-0.3 mM. Here, as the amphoteric phospholipid anionic phospholipid cholesterol cationic phospholipid:disulfide-group-containing lipid, DPPC:DCP: cholesterol:DPPE:sPDP may be used, and preferably, DPPC:DCP:cholesterol:DPPE:sPDP are mixed at a ratio of 2.0 mM:0.18 mM:0.9 mM:0.17 mM:0.17 mM.

The DSPE-PEG-sPDP lipid in the microbubble is used as a crosslinking agent when the microbubble is conjugated to the nanoliposome, thus forming a nanoliposome-microbubble conjugate.

The microbubble may result from bubbling of the mixture of the amphoteric phospholipid, the anionic phospholipid, cholesterol, the cationic phospholipid and the disulfide-group-containing lipid. The inside of the microbubble may be filled with a hydrophobic gas selected from among $SF_6$, $CO_2$, $CF_4$ and $C_3F_8$. The hydrophobic gas is preferably $SF_6$.

The nanoliposome may have a particle size of 100 to 200 nm. If the size of the nanoliposome is less than 100 nm, it is difficult to encapsulate the drug for hair loss treatment into the nanoliposome, and the stability thereof may decrease upon in-vivo injection, which is undesirable. On the other hand, if the size thereof exceeds 200 nm, the composition including the nanoliposome may be decreased in stability upon in-vivo injection, which is undesirable. Also, the microbubble may have a particle size of 1000 to 2000 nm. Accordingly, the nanoliposome-microbubble conjugate may have a particle size of about 1100 to 2200 nm.

The present invention may provide a composition for alleviating or treating hair loss containing the nanoliposome-microbubble conjugate composition. The nanoliposome-microbubble conjugate composition is effective at treating hair loss by inhibiting the male hormone 5a reductase and thus lowering the concentration of dihydrotestosterone (DHT).

In the method of preparing the nanoliposome-microbubble conjugate composition according to the present invention, the nanoliposome is prepared, the microbubble is prepared, and the nanoliposome and the microbubble are mixed, thereby yielding a conjugate.

In the preparation of the nanoliposome, lecithin, cholesterol and the cationic phospholipid in step 1 may be mixed at a molar ratio of 2:0.01-0.5:0.01-0.5. If the mixing ratio thereof falls out of the above range, it is difficult to prepare the lipid that constitutes the nanoliposome.

In step 2, the drug for hair loss treatment may be added at a concentration of 0.01 to 1000 ng/ml to the lipid film composition. The solvent for the drug solution for hair loss treatment may be water or alcohol. Here, the alcohol is preferably ethanol or an aqueous solution thereof.

The freezing and thawing in step 3 may be repeated 1 to 12 times. When the process of freezing and thawing the lipid film composition is repeated in this way, a nanoliposome dispersion solution having a more uniform size may be formed, and the drug encapsulation efficiency of the nanoliposome may increase. If the number of times the process is repeated exceeds 12, the encapsulation efficiency of the nanoliposome may decrease. Hence, the above process is preferably performed 12 times or less.

For conjugation of the nanoliposome to the microbubble, the microbubble may be stabilized using at least one solution among a glucose solution, glycerol and propylene glycol in step B during the preparation of the microbubble according to the present invention, and may then be mixed with the nanoliposome. Preferably, a glucose solution is used. Here, the glucose solution may have a concentration of 1 to 20% (w/v). If the concentration of glucose exceeds 20% (w/v), the resulting solution may become viscous, making it impossible to synthesize the microbubble.

The present invention may provide a pharmaceutical composition containing the nanoliposome-microbubble conjugate. The pharmaceutical composition of the present invention may be formulated into oral dosage forms, such as powder, granule, tablet, capsule, suspension, emulsion, syrup, and aerosol formulations, as well as formulations for external use, suppositories, and sterile injectable solutions, in accordance with typical individual processes. A carrier, an excipient and a diluent that may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. The formulation may be typically prepared using a diluent or excipient such as a filler, an extender, a binder, a wetting agent, a disintegrant, a surfactant, and the like. A solid formulation for oral administration may include tablets, pills, powders, granules, capsules, and the like, and such a solid formulation may be prepared by mixing the composition of the present invention with at least one excipient, for example starch, calcium carbonate, sucrose, lactose, gelatin, and the like. In addition to the simple excipient, lubricants such as magnesium stearate, talc and the like may be used. An oral liquid formulation may include suspensions, solutions, emulsions, syrups, and the like, and may also include not only simple diluents, such as water or liquid paraffin, but also various excipients, for example, wetting agents, sweeteners, fragrances, preservatives, etc. A formulation for parenteral administration may include sterilized aqueous solutions, non-aqueous solvents, suspensions, emulsions, freeze-dried preparations and suppositories. As non-aqueous solvents or suspension agents, propylene glycol, polyethylene glycol, vegetable oil such as olive oil, injectable esters such as ethyl oleate and the like may be used. As the base of a suppository, Witepsol, Macrogol, Tween 61, cacao butter, laurin fat, glycerogelatin and the like may be used.

The amount of the pharmaceutical composition according to the present invention, when administered, may vary depending on the age, gender and weight of the subject to be treated, the particular disease or pathological condition for treatment, the severity of the disease or pathological condition, the administration route and the judgment of the prescriber. A dose determination based on these factors will be apparent to those skilled in the art, and the dose typically falls in the range of 0.01 mg/kg/day to about 2000 mg/kg/day. Preferably, the dose is set to the range of 1 mg/kg/day to 500 mg/kg/day. Administration may be carried out once a day or several times a day. The dose does not in any way limit the scope of the present invention.

The pharmaceutical composition of the present invention may be administered to mammals including mice, livestock, humans, and the like, through various routes. All modes of administration, for example, through the skin application, orally, or through intrarectal, intravenous, intramuscular, subcutaneous, intraperitoneal or intracerebroventricular injection, may be considered.

Advantageous Effects

The present invention pertains to a nanoliposome-microbubble conjugate in which a drug for hair loss treatment such as finasteride, minoxidil, dutasteride, etc. is encapsulated in a nanoliposome and to a composition for alleviating or treating hair loss containing the same. An orally administered agent such as finasteride currently useful as the drug for hair loss treatment causes various side effects when administered orally, and thus drug delivery through scalp application is regarded as most desirable, but the drug itself is not delivered well to hair follicle cells through scalp application alone. In addition, a drug for hair loss treatment useful as an external preparation for skin causes various side effects, and therefore the concentration thereof that is used needs to be further lowered.

Accordingly, it is important to increase the drug delivery efficiency of finasteride using a delivery support. The use of the nanoliposome-microbubble conjugate of the present invention is capable of increasing the delivery efficiency of the drug for hair loss treatment at a low concentration, making it possible to effectively treat androgenic alopecia.

Korean Patent No. 10-1683463 discloses an intracellular drug delivery technique using microbubbles, but it is limited only to technologies that can be applied to anticancer drugs. Korean Patent No. 10-1054731 discloses nanoparticles including finasteride and an external preparation composition for skin containing the same, but the structure of the nanoliposome thereof is different from the present invention, from which it can be confirmed that the present invention is different from the above techniques.

BRIEF DESCRIPTION OF DRAWINGS

FIG. 1 schematically shows a process by which, when a nanoliposome-microbubble conjugate of the present invention is delivered to dermal papilla cells (DPCs) and sonication is performed, the cell membrane is perforated and the microbubble collapses, whereby the nanoliposome enters the cells;

FIG. 2 shows a Cryo-EM image of a liposome having a size of 200 nm or less (left) and an optical microscope image of a bubble having a size of 1 to 2 to (right);

FIG. 3 is a photograph showing the intracellular penetration of the drug (including fluorophore) through the nanoliposome-microbubble conjugate (HTP) (right) and a photograph showing the control cells therefor (left), in which the photograph above the cell photograph is an ultrasound image of the microbubble (HTP);

FIG. 4 is a graph showing the cytotoxicity of DPCs upon treatment of 3T3 cells and DPCs with testosterone (TS) (left), and a graph showing almost no cytotoxicity upon treatment of DPCs with HTP alone or with both HTP and testosterone (TS) (right);

FIG. 5 is photographs showing the results of measurement of hair growth effects at an interval of one week after inducing hair loss in mice and then treating the mice five times with the nanoliposome-microbubble conjugate (HTP) of the present invention (Control: group not treated with drug, TS: testosterone, HTS: nanoliposome-microbubble of Example 1, NL: liposome of Comparative Example 1).

MODE FOR INVENTION

A better understanding of the present invention will be given through the following examples. However, the present invention is not limited to the examples described herein, and may be embodied in other forms. Furthermore, the examples are set forth to provide those skilled in the art with an understanding of the spirit of the present invention so that the teachings herein are thorough and complete.

Example 1. Production of Nanoliposome-Microbubble Conjugate

Example 1-1. Production of Nanoliposome

Lecithin (Sigma Aldrich), cholesterol (Sigma Aldrich) and DPPE (Sigma Aldrich) as a cationic phospholipid were mixed at a molar ratio of 2:0.1:0.05 in chloroform and then formed into a lipid film using a rotary evaporator.

The lipid film was added with finasteride and mixed through sonication. A freezing and thawing cycle using liquid nitrogen was repeated five times, and then sonication (probe mode) was performed, thus preparing a uniform nanoliposome composition having a smaller size.

Thereafter, the nanoliposome composition (total amount of lipid: 20.43 mg) precipitated through centrifugation was recovered and dispersed in a 5% (w/v) glucose aqueous solution. The finasteride concentration in each of the finasteride solution before the preparation of nanoliposome and the solution remaining after the preparation of nanoliposome was measured, and thus the drug encapsulation efficiency in the nanoliposome was found to be 60% or more.

Example 1-2. Production of Microbubble 15.4 mg of DPPC (1,2-dipalmitoyl-sn-glycero-3-phosphocholine, Sigma Aldrich) as an amphoteric phospholipid, 3.48 mg of cholesterol (Sigma Aldrich), 1 mg of DCP (dicetyl phosphate, Sigma Aldrich) as an anionic phospholipid, 1.2 mg of DPPE (1,2-dipalmitoyl-sn-glycero-3-phosphoethanolamine, Sigma Aldrich) as a cationic phospholipid, and 5 mg of DSPE-PEG-sPDP (1,2-distearoyl-sn-phosphoethanolamine-N-[PDP (polyethylene glycol)], Avanti polar) as a disulfide-group-containing lipid were mixed in 1 ml of chloroform and then formed into a lipid film for microbubble synthesis using a rotary evaporator.

Thereafter, 1 ml of a 5% (w/v) glucose aqueous solution was added thereto and mixed therewith through sonication. A freezing and thawing cycle using liquid nitrogen was repeated three times, and sonication (probe mode) and then filling with an $SF_6$ gas were conducted, thereby preparing a microbubble composition in a dispersed phase.

Example 1-3. Formation of Nanoliposome-Microbubble 1 ml of the nanoliposome (20.53 mg/ml) prepared in Example 1-1 and 0.5 ml of the microbubble (26.08 mg/ml) of Example 1-2 were mixed (at a volume ratio of 2:1), whereby the nanoliposome and the microbubble were dispersed in the glucose aqueous solution.

Thereafter, strong vibration [Mixing frequency: 4500 tr/mn (cpm: $m^3$ per min)] was applied for 15 sec using a machine (Tianjin Iris), thus forming a nanoliposome-microbubble conjugate, which was then refrigerated in the state of being dispersed in a 5% glucose aqueous solution.

The nanoliposome-microbubble conjugate thus obtained is referred to as a 'nanoliposome-microbubble conjugate of Example 1' or a hair loss therapeutic particle (HTP).

Comparative Example 1. Nanoliposome

A nanoliposome (not conjugated with a microbubble) was prepared in the same manner as in Example 1-1, and was used as the composition of Comparative Example 1.

Experimental Example 1. Evaluation of Size and Surface Charge of Nanoliposome-Microbubble Conjugate The nanoliposome and the microbubble produced in Examples 2-1 and 2-2 are imaged and shown in FIG. 2. The left image of FIG. 2 shows the nanoliposome and the right image thereof shows the microbubble, indicating that each was prepared at an appropriate size.

The size of the nanoliposome-microbubble conjugate formed by conjugating the nanoliposome and the microbubble was measured through dynamic light scattering (DLS), and the average size thereof was about 1100 nm and the surface charge was +2.25 mV. The size of the nanoliposome alone of Comparative Example 1 (Example 1-1), not conjugated with the microbubble, was 98 nm, and the surface charge thereof was +1.75 mV. In order to deliver the nanoliposome into dermal papilla cells, a positive surface charge is preferable. Although the surface charge of the microbubble conjugate alone was −0.91 mV, the surface charge of the nanoliposome-microbubble conjugate of the present invention was not lowered but had a positive charge of greater magnitude. Therefore, the nanoliposome-microbubble conjugate of the present invention was concluded to be suitable for use as a cell delivery composition.

Experimental Example 1. Evaluation of Cell Survival and Penetration

In order to evaluate the entry of the nanoliposome-microbubble conjugate of Example 1 into the dermal papilla cells, DPCs were treated for 2 hr with the nanoliposome-microbubble conjugate of Example 1 at a finasteride concentration of 100 ng/ml. The confocal fluorescent microscope image thereof is shown in FIG. 3. Here, during the production of the nanoliposome-microbubble conjugate, the nanoliposome lipid was introduced with a fluorophore RITC (red) dye and observed.

In FIG. 3, the blue shows a DNA-stained image and the red shows a fluorescent image of RITC. No red is observed in the control group, but the red in the cytoplasm and the blue in the nucleus (DNA) appear merged in the right image. Therefore, it can be found that the nanoliposome including finasteride encapsulated therein was efficiently introduced into DPCs due to the treatment with the nanoliposome-microbubble conjugate of Example 1.

Moreover, the state in which the microbubble was wholly conjugated to the nanoliposome-microbubble conjugate (HTP) was observed through ultrasound imaging, and it was confirmed that a brown band due to the microbubble appeared in the HTP solution (the top photograph of FIG. 3).

Experimental Example 3. Evaluation of Cell Viability

Cell viability was evaluated through WST-1 assay (EZ-cytox Cell Viability Assay Kit). DPCs and 3T3 fibroblasts were cultured at a density of $1 \times 10^4$/well in a 96-well plate for 24 hr. Here, the culture medium was replaced with a new medium containing 200 µM testosterone, and after 24 hr, a WST-1 reagent was added thereto. The WST-1 reagent was added in an amount of 10% of the culture broth, and after 1 hr, absorbance was measured at 460 nm and thus cell survival and proliferation were compared with a control group (non-treated group). Cell survival was measured at an interval of 24 hr for 4 days after testosterone treatment.

These results are shown in the left of FIG. 4. The extent of apoptosis over time was greatly increased in DPCs compared to 3T3 cells, indicating that a model of hair loss with an increase in the amount of testosterone was well established.

After treatment with the nanoliposome-microbubble conjugate (HTP) of the present invention before treatment with testosterone in the same manner, the culture medium was replaced with a new medium containing 200 µM testosterone, the subsequent procedures were conducted as above, and the state of cells was observed. A comparative group was treated with the nanoliposome-microbubble conjugate (HTP) alone.

As is apparent from the right graph of FIG. 4, the cells grew well without toxicity in the group treated with the nanoliposome-microbubble conjugate (HTP) alone or the group treated with both the nanoliposome-microbubble conjugate and testosterone (TS+HTP).

These results showed that finasteride was well encapsulated in the nanoliposome-microbubble conjugate of Example 1 of the present invention and thus the functionality of the above drug was capable of being optimally exhibited, and also that the above conjugate was able to effectively inhibit hair loss due to apoptosis by testosterone in the dermal papilla cells.

Experimental Example 4. Evaluation of Effect of Nanoliposome-Microbubble Conjugate on Inhibiting Hair Loss in Mouse Model The hair on the back of each of 6-week-old mice (C57BL/6J) was epilated using an animal epilator (Philips) and hair removal cream (Veet), after which testosterone was dissolved in a mixed solution of propylene glycol and ethanol (3:7 (v:v)) and applied every day at a concentration of 30 µg/ml, and thus an environment similar to that of human hair loss was made.

In the present experiment, the individual test groups were as follows (testosterone was applied to the skin in all cases).

① A control group (non-treated group);

② A group treated with testosterone;

③ A group treated with testosterone and then subjected to skin application with the nanoliposome-microbubble conjugate of Example 1;

④ A group treated with testosterone and then subjected to oral administration with a commercially available finasteride solution;

⑤ A group treated with testosterone and then subjected to skin application with a commercially available finasteride solution;

⑥ A group treated with testosterone and then subjected to skin application with the nanoliposome of Comparative Example 1; and ⑦ A group subjected to skin application with the nanoliposome-microbubble conjugate of Example 1.

A nanoliposome-microbubble conjugate (HTP) configured such that the nanoliposome and the microbubble were conjugated and dispersed at a ratio of 2:1 was used. 200 µl thereof, having a total finasteride content of 1 µg, was applied on the entire epilated back of the mice using a plastic spatula, and after 3 min, was exposed to ultrasound using a medical sonicator. Here, the nanoliposome-microbubble conjugate was applied five times at an interval of one day. Under the same conditions, the total finasteride content was matched in the group treated with the commercially available finasteride solution in lieu of the solution of Example 1 or Comparative Example 1.

Since the commercially available finasteride solution is an orally administered agent, it was administered in a dose 10 times that of the application dose in the oral administration group for comparison, and the administration time and the number of administrations were set the same as for the skin application.

The results thereof are shown in FIG. 5. In FIG. 5, Control is a group not treated with the drug, TS represents testosterone, HTS represents the nanoliposome-microbubble of Example 1, and NL represents the liposome of Comparative Example 1.

Referring to the results of FIG. 5, the control group ① did not undergo any treatment and hair grew naturally over time, and the group ② treated with testosterone alone grew hardly any hair.

On the other hand, in the group ③ treated with testosterone and then with the composition of Example 1, it was confirmed that hair grew well.

In contrast, in the group ④ treated with testosterone and then subjected to oral administration with the commercially available finasteride drug or the group ⑤ treated with testosterone and then subjected to skin application with the commercially available finasteride drug, the hair started growing on the seventh week.

In the group ⑥ treated with testosterone and then with the liposome of Comparative Example 1, not conjugated with the microbubble, hardly any hair grew, like the comparative group treated with testosterone alone. This was confirmed because the drug for hair loss treatment is encapsulated in the liposome and thus the in-vivo delivery ability thereof is lower than that of the commercially available drug. These results demonstrate that it is essential that the liposome be transported into the biomembrane through the microbubble so that the drug is delivered.

Although not shown in the photographs of FIG. 5, the hair also grew in the group treated with the composition (HTP) alone of Example 1 like the control group, and thus, side effects such as special toxicity, etc. did not appear.

Therefore, the above results suggest that the nanoliposome-microbubble conjugate of the present invention is very effective at treating androgenic alopecia.

The invention claimed is:

1. A composition for alleviating hair loss comprising a nanoliposome-microbubble conjugate consisting of a nanoliposome, a microbubble filled with a hydrophobic gas and a drug for hair loss treatment, wherein the drug for hair loss treatment is encapsulated in the nanoliposome, wherein the drug for hair loss treatment is at least one selected from the group consisting of finasteride, minoxidil and dutasteride, wherein the nanoliposome consists of (a) lecithin, (b) cholesterol and (c) a phosphatidylethanolamine phospholipid which is at least one selected from the group consisting of dioleoyl phosphatidylethanolamine (DOPE), 1,2-diphytanoyl-sn-glycero-3-phosphoethanolamine (DPhPE), 1,2-distearoyl-sn-glycero-3-phosphoethanolamine (DSPE), and 1,2-dipalmitoyl-sn-glycero-3-phosphoethanolamine (DPPE), and wherein the microbubble consists of (1) an amphoteric phospholipid which is at least one selected from the group consisting of 1,2-dipalmitoyl-sn-glycero-3-phosphocholine (DPPC), 1,2-distearoyl-sn-glycero-3-phosphocholine (DSPC), 1,2-dimyristoyl-sn-glycero-3-phosphocholine (DMPC), 1,2-dioleoyl-sn-glycero-3-phosphocholine (DOPC), 1-myristoyl-2-palmitoyl-sn-glycero-3-phosphocholine (MPPC) and 1-myristoyl-2-stearoyl-sn-glycero-3-phosphocholine (MSPC), (2) an anionic phospholipid which is at least one from the group consisting of selected from the group consisting of dicetyl phosphate (DCP), 1,2-dierucoyl-sn-glycero-3-phosphate (DEPA), 1,2-dilauroyl-sn-glycero-3-phosphate (DLPA), 1,2-dimyristoyl-sn-glycero-3-phosphate (DMPA) and 1,2-dioleoyl-sn-glycero-3-phosphate (DOPA), (3) cholesterol, (4) a phosphatidylethanolamine phospholipid which is at least one selected from the group consisting of dioleoyl phosphatidylethanolamine (DOPE), 1,2-diphytanoyl-sn-glycero-3-phosphoethanolamine (DPhPE), 1,2-distearoyl-sn-glycero-3-phosphoethanolamine (DSPE), and 1,2-dipalmitoyl-sn-glycero-3-phosphoethanolamine (DPPE), and (5) 1,2-distearoyl-sn-glycero-3-phosphoethanolamine-N-poly(ethylene glycol)-2000-N-[3-(2-pyridyldithio)propionate (DSPE-PEG-sPDP).

2. The composition of claim 1, wherein the drug for hair loss treatment inhibits expression or activity of 5-alpha reductase type 2 to thus prevent conversion of testosterone into dihydrotestosterone, or inhibits death of dermal papilla cells.

3. The composition of claim 1, wherein the amphoteric phospholipid in the microbubble is 1-myristoyl-2-palmitoyl-sn-glycero-3-phosphocholine (MPPC) or 1-myristoyl-2-stearoyl-sn-glycero-3-phosphocholine (MSPC).

4. The composition of claim 1, wherein the molar ratio of lecithin to cholesterol to phosphatidylethanolamine in the nanoliposome is 2:0.1:0.5.

5. The composition of claim 1, wherein the amphoteric phospholipid in the microbubble is 1,2-dipalmitoyl-sn-glycero-3-phosphocholine (DPPC).

6. The composition of claim 1, wherein the anionic phospholipid in the microbubble is dicetyl phosphate (DCP).

7. The composition of claim 1, wherein the phosphatidylethanolamine in the microbubble is 1,2-dipalmitoyl-sn-glycero-3-phosphoethanolamine (DPPE).

8. The composition of claim 1, wherein the amphoteric phospholipid in the microbubble is 1,2-dipalmitoyl-sn-glycero-3-phosphocholine (DPPC), the anionic phospholipid in the microbubble is dicetyl phosphate (DCP), and the phosphatidylethanolamine in the microbubble is 1,2-dipalmitoyl-sn-glycero-3-phosphoethanolamine (DPPE).

9. The composition of claim 8, wherein the molar ratio of lecithin to cholesterol to phosphatidylethanolamine in the nanoliposome is 2:0.1:0.5.

10. The composition of claim 1, wherein the hydrophobic gas is selected from the group consisting of $SF_6$, $CO_2$, $CF_4$ and $C_3F_8$.

11. The composition of claim 1, wherein the hydrophobic gas is $SF_6$.

\* \* \* \* \*